United States Patent
Vizesi et al.

(10) Patent No.: US 12,311,076 B1
(45) Date of Patent: May 27, 2025

(54) DEMINERALIZED BONE MATRIX COMPOSITION WITH ENHANCED OSTEOINDUCTIVITY AND OSTEOCONDUCTIVITY

(71) Applicant: Seaspine, Inc., Carlsbad, CA (US)

(72) Inventors: Frank Vizesi, Carlsbad, CA (US); Scott David Boden, Carlsbad, CA (US); Tyler Paul Lipschultz, Carlsbad, CA (US); Michelle Esplago Pacer, Carlsbad, CA (US); Doo Wan Kim, Carlsbad, CA (US)

(73) Assignee: Seaspine, Inc., Carlsbad, CA (US)

( * ) Notice: Subject to any disclaimer, the term of this patent is extended or adjusted under 35 U.S.C. 154(b) by 1126 days.

(21) Appl. No.: 16/433,668

(22) Filed: Jun. 6, 2019

Related U.S. Application Data (60) Provisional application No. 62/681,842, filed on Jun. 7, 2018.

(51) Int. Cl.
*A61L 27/36* (2006.01)

(52) U.S. Cl.
CPC ....... *A61L 27/3608* (2013.01); *A61L 27/3691* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 4,394,370 A | 7/1983 | Jefferies | |
| 4,440,750 A | 4/1984 | Glowacki et al. | |
| 4,472,840 A | 9/1984 | Jefferies | |
| 5,162,114 A | 11/1992 | Kuberasampath et al. | |
| 5,507,813 A | 4/1996 | Dowd et al. | |
| 5,573,771 A | 11/1996 | Geistlich et al. | |
| 5,607,269 A * | 3/1997 | Dowd | B23Q 11/0825 29/DIG. 56 |
| 5,707,962 A | 1/1998 | Chen et al. | |
| 6,165,487 A | 12/2000 | Ashkar et al. | |
| 6,180,606 B1 | 1/2001 | Chen et al. | |
| 6,189,537 B1 | 2/2001 | Wolfinbarger | |
| 6,305,379 B1 | 10/2001 | Wolfinbarger | |
| 6,326,018 B1 | 12/2001 | Gertzman et al. | |
| 6,436,138 B1 | 8/2002 | Dowd et al. | |
| 6,458,375 B1 | 10/2002 | Gertzman et al. | |
| 6,616,698 B2 | 9/2003 | Scarborough | |
| 6,630,153 B2 | 10/2003 | Long et al. | |
| 6,632,247 B2 | 10/2003 | Boyer et al. | |
| 6,685,626 B2 | 2/2004 | Wironen | |
| 6,808,585 B2 | 10/2004 | Boyce | |
| 6,953,594 B2 | 10/2005 | Lee et al. | |
| 7,163,691 B2 | 1/2007 | Knaack et al. | |
| 7,291,345 B2 | 11/2007 | Winterbottom et al. | |
| 7,323,193 B2 | 1/2008 | Morris et al. | |
| 7,498,040 B2 | 3/2009 | Masinaei et al. | |
| 7,498,041 B2 | 3/2009 | Masinaei et al. | |
| 7,517,539 B1 | 4/2009 | Lee et al. | |
| 7,582,309 B2 | 9/2009 | Rosenberg et al. | |
| 7,621,963 B2 | 11/2009 | Simon et al. | |
| 7,744,597 B2 | 6/2010 | Gaskins et al. | |
| 7,749,555 B2 | 7/2010 | Zanella et al. | |
| 7,766,972 B2 | 8/2010 | Overby et al. | |
| 7,771,741 B2 | 8/2010 | Drapeau et al. | |
| 7,939,108 B2 | 5/2011 | Morris et al. | |
| 7,959,683 B2 | 6/2011 | Semler et al. | |
| 7,959,941 B2 | 6/2011 | Knaack et al. | |
| 7,985,414 B2 | 7/2011 | Knaack et al. | |
| 8,039,021 B2 | 10/2011 | Royer | |
| 8,133,421 B2 | 3/2012 | Boyce et al. | |
| 8,202,539 B2 | 6/2012 | Behnam et al. | |
| 8,221,781 B2 | 7/2012 | Rosenberg et al. | |
| 8,268,008 B2 | 9/2012 | Betz et al. | |
| 8,309,106 B2 | 11/2012 | Masinaei et al. | |
| 8,323,700 B2 | 12/2012 | Morris et al. | |
| 8,333,985 B2 | 12/2012 | Knaack et al. | |
| 8,357,384 B2 | 1/2013 | Behnam et al. | |
| 8,372,157 B2 | 2/2013 | Petersen et al. | |
| 8,435,566 B2 | 5/2013 | Behnam et al. | |
| 8,454,988 B2 | 6/2013 | Rosenberg et al. | |
| 8,475,824 B2 | 7/2013 | McKay | |
| 8,506,983 B2 | 8/2013 | Mohan et al. | |
| 8,529,962 B2 | 9/2013 | Morris | |
| 8,613,938 B2 | 12/2013 | Akella et al. | |

(Continued)

FOREIGN PATENT DOCUMENTS

| | | |
|---|---|---|
| CA | 1339083 | 7/1997 |
| CA | 2291718 | 12/1998 |
| CA | 2027259 | 12/2000 |
| CA | 2403672 | 9/2001 |
| CA | 2540969 | 11/2005 |
| CA | 2243365 | 7/2006 |
| CA | 2177017 | 4/2008 |
| CA | 2446400 | 4/2009 |
| CA | 2430744 | 11/2009 |
| CA | 2423603 | 5/2010 |
| CA | 2745038 | 5/2010 |
| CA | 2415061 | 11/2010 |

(Continued)

*Primary Examiner* — David J Blanchard
*Assistant Examiner* — Daniel F Coughlin
(74) *Attorney, Agent, or Firm* — Dinsmore & Shohl LLP

(57) ABSTRACT

An osteoinductive and osteoconductive composition including DBM fibers having multiple geometries, as well as a method of producing the same are disclose. For example, such a method may include: obtaining bone tissue; cleaning the bone tissue obtained with a plurality of washes; milling the cleaned bone tissue into a plurality of fibers of two or more geometries including a long wide fiber, a long narrow fiber, a short wide fiber, and a short narrow fiber; demineralizing the plurality of fibers of two or more geometries to expose one or more biologically active components; and neutralizing the plurality of demineralized fibers of two or more geometries resulting in demineralized bone matrix.

9 Claims, 4 Drawing Sheets

(56) References Cited

U.S. PATENT DOCUMENTS

| | | |
|---|---|---|
| 8,663,672 B2 | 3/2014 | Manrique et al. |
| 8,753,689 B2 | 6/2014 | Morris et al. |
| 8,758,438 B2 | 6/2014 | Boyce et al. |
| 8,758,792 B2 | 6/2014 | Behnam et al. |
| 8,911,759 B2 | 12/2014 | Behnam |
| 8,926,710 B2 | 1/2015 | McKay |
| 9,029,077 B2 | 5/2015 | Song et al. |
| 9,034,358 B2 | 5/2015 | Behnam et al. |
| 9,066,994 B2 | 6/2015 | Scarborough |
| 9,072,817 B2 | 7/2015 | Song et al. |
| 9,107,751 B2 | 8/2015 | Winterbottom et al. |
| 9,162,012 B2 | 10/2015 | Benham et al. |
| 9,198,758 B2 | 12/2015 | McKay |
| 9,241,797 B2 | 1/2016 | McKay |
| 9,308,295 B2 | 4/2016 | Carter et al. |
| 9,364,583 B2 | 6/2016 | McKay |
| 9,381,272 B2 | 7/2016 | Lacza et al. |
| 9,387,094 B2 | 7/2016 | Manrique et al. |
| 2001/0014667 A1 | 8/2001 | Chen et al. |
| 2001/0018614 A1 | 8/2001 | Bianchi |
| 2001/0038848 A1 | 11/2001 | Donda et al. |
| 2003/0055511 A1 | 3/2003 | Schryver et al. |
| 2003/0055512 A1 | 3/2003 | Genin et al. |
| 2003/0135214 A1 | 7/2003 | Fetto et al. |
| 2004/0019132 A1 | 1/2004 | Long et al. |
| 2005/0131548 A1 | 6/2005 | Boyer et al. |
| 2005/0281856 A1 | 12/2005 | McGlohom et al. |
| 2006/0083769 A1 | 4/2006 | Kumar et al. |
| 2006/0233849 A1 | 10/2006 | Simon et al. |
| 2008/0091270 A1 | 4/2008 | Miller et al. |
| 2009/0234277 A1 | 9/2009 | Wei et al. |
| 2010/0196333 A1 | 8/2010 | Gaskins et al. |
| 2010/0297082 A1 | 11/2010 | Guelcher et al. |
| 2012/0082704 A1 | 4/2012 | Phillips et al. |
| 2013/0189338 A1 | 7/2013 | Drapeau et al. |
| 2013/0195805 A1 | 8/2013 | Wei et al. |
| 2013/0274890 A1 | 10/2013 | McKay |
| 2013/0297038 A1 | 11/2013 | McKay |
| 2014/0205674 A1 | 7/2014 | Wei |
| 2014/0212471 A1 | 7/2014 | Drapeau et al. |
| 2014/0212499 A1 | 7/2014 | Cooper et al. |
| 2014/0220142 A1 | 8/2014 | Song et al. |
| 2014/0277570 A1 | 9/2014 | Behnam et al. |
| 2014/0314822 A1 | 10/2014 | Carter et al. |
| 2015/0057664 A1* | 2/2015 | Scianamblo ............ B28D 1/14 606/80 |
| 2015/0093429 A1 | 4/2015 | Carter et al. |
| 2015/0140096 A1 | 5/2015 | Malinin |
| 2015/0182667 A1 | 7/2015 | Guelcher et al. |
| 2015/0251361 A1 | 9/2015 | Meyer et al. |
| 2015/0258245 A1 | 9/2015 | Behnam et al. |
| 2015/0328003 A1 | 11/2015 | Samaniego et al. |
| 2015/0343114 A1 | 12/2015 | Drapeau et al. |
| 2015/0343116 A1 | 12/2015 | Carter et al. |
| 2016/0081803 A1 | 3/2016 | McKay |
| 2016/0135954 A1 | 5/2016 | Schlachter et al. |
| 2016/0136329 A1 | 5/2016 | Schlachter et al. |

FOREIGN PATENT DOCUMENTS

| | | |
|---|---|---|
| CA | 2404683 | 2/2011 |
| CA | 2416481 | 2/2011 |
| CA | 2363153 | 4/2011 |
| CA | 2438192 | 7/2011 |
| CA | 2457372 | 12/2011 |
| CA | 2528086 | 1/2013 |
| CA | 2637606 | 3/2013 |
| CA | 2619469 | 3/2015 |
| CA | 2925584 | 4/2015 |
| EP | 419275 | 1/1995 |
| EP | 489728 | 1/1997 |
| EP | 732947 | 3/2002 |
| EP | 1296726 | 2/2004 |
| EP | 1140239 | 7/2004 |
| EP | 1301222 | 12/2005 |
| EP | 880345 | 4/2006 |
| EP | 1152777 | 5/2006 |
| EP | 1341484 | 5/2009 |
| EP | 2211921 | 12/2013 |
| WO | 2010050935 | 5/2010 |
| WO | 2015054547 | 4/2015 |
| WO | 2016044495 | 3/2016 |
| WO | 2016123583 | 8/2016 |

* cited by examiner

DEMINERALIZED BONE MATRIX COMPOSITION WITH ENHANCED OSTEOINDUCTIVITY AND OSTEOCONDUCTIVITY

BACKGROUND

Conventionally, the mechanism of bone formation of a demineralized bone matrix (hereinafter "DBM") is the osteoinductive potential of the DBM, which is the release of native bone proteins such as bone morphogenetic proteins (hereinafter "BMPs") from the collagenous matrix of the bone tissue. These native growth factors are normally in the bone tissue, but are substantially unavailable for release from the matrix because they are trapped within the mineral component of the bone. Osteoinductivity is achieved by removing the mineral component of the bone (e.g. demineralizing), which is typically done through an acid washing step. This demineralization leaves behind a collagen matrix and the various growth factors that may now be readily released in vivo. It is known in the art that osteoinductivity of the DBM may be affected by the demineralization process and the extent of demineralization; and as such the osteoinductive potential may be affected in a variety of ways including, but not limited to, the strength of the acid, the ratio of acid to bone, temperature, stirring/agitation, time, and potentially the size/shape of the bone particles.

Another mechanism of bone formation of a demineralized bone matrix is osteoconduction, which is the ability of DBM material to act as a scaffold for new bone formation. Traditionally, DBMs are usually considered to be weakly osteoconductive. There is a need in the art to capitalize on both the osetoinductive and osteoconductive properties of DBM, such that a DBM product for in vivo use may optimize the overall bone forming response with elements of both osteoinduction and osteoconduction.

SUMMARY

In one aspect a method of producing an osteoinductive and osteoconductive composition for in vivo use is disclosed. Such a method includes: obtaining bone tissue; cleaning the bone tissue obtained with a plurality of washes; milling the cleaned bone tissue into a plurality of fibers of two more geometries, where the two or more geometries include: a long wide fiber, a long narrow fiber, a short wide fiber, and a short narrow fiber; and demineralizing the plurality of fibers of two or more geometries to expose one or more biologically active components.

In some embodiments, the milling is performed on a CNC machine using a solid carbide 2-straight flute end mill at a range from about 1500 rpm to about 2500 rpm with a feed rate of about 0.38 mm per circumferential pass.

In some embodiments, the long wide fiber has a length of about 10 mm or greater and a width between about 0.6 mm and about 1.0 mm. In other embodiments, the long wide fiber has a length between about 10 mm and about 50 mm, and a width of about 0.8 mm.

In some embodiments, the long narrow fiber has a length of about 10 mm or greater and a width between about 0.2 mm and about 0.6 mm. In other embodiments, the long narrow fiber has a length between about 10 mm and about 50 mm and a width of about 0.4 mm.

In some embodiments, the short wide fiber has a length of less than about 10 mm and a width between about 0.6 mm and about 1.0 mm. In other embodiments, the short wide fiber has a length of less than about 10 mm and a width of about 0.8 mm.

In some embodiments, the short narrow fiber has a length of less than about 10 mm and a width between about 0.2 mm and about 0.6 mm. In other embodiments, the short narrow fiber has a length of less than about 10 mm and a width of about 0.4 mm.

In some embodiments, the method further includes freeze-drying the plurality of demineralized fibers of two or more geometries. In other embodiments, the method further includes neutralizing the plurality of demineralized fibers of two or more geometries resulting in demineralized bone matrix.

In some embodiments, the demineralizing fibers of two or more geometries includes treating the plurality of fibers with a hydrochloric acid treatment.

In another aspect, an oseteoinductive and osteoinductive composition including demineralized bone matrix is disclosed, where the demineralized bone matrix includes two or more fiber geometries selected from a group consisting of: long wide fibers; long narrow fibers; short wide fibers; and short narrow fibers.

In yet another aspect, an oseteoinductive and osteoinductive composition including demineralized bone matrix is disclosed, where the demineralized bone matrix comprises two or more fiber geometries selected from a group consisting of: long wide fibers with a length of about 10 mm or greater and a width between about 0.6 mm and about 1.0 m; long narrow fibers with a length of about 10 mm or greater and a width between about 0.2 mm and about 0.6 mm; short wide fibers with a length of less than about 10 mm and a width between about 0.6 mm and about 1.0 mm; and short narrow fibers with a length of less than about 10 mm and a width between about 0.2 mm and about 0.6 mm.

In another aspect, an oseteoinductive and osteoinductive composition comprising demineralized bone matrix is disclosed, where the demineralized bone matrix comprises a mixture of long wide fibers and long narrow fibers; where the long wide fibers have a length of about 10 mm or greater and a width between about 0.6 mm and about 1.0 m, and where the long narrow fibers have a length of greater than about 10 mm and a width between about 0.2 mm and about 0.6 mm.

In still another aspect, an osteoinductive and osteoconductive composition including demineralized bone matrix is disclosed, where the demineralized bone matrix comprises a mixture of long wide fibers and long narrow fibers at a ratio of about 65:35; where the long wide fibers have a length of about 10 mm or greater and a width between about 0.6 mm and about 1.0 mm, and where the long narrow fibers have a length of about 10 mm or greater and a width between about 0.2 mm and about 0.6 mm.

In still yet another aspect, an osteoinductive and osteoconductive composition including demineralized bone matrix is disclosed, where the demineralized bone matrix comprises a mixture of long wide fibers having a length of about 30 mm to about 50 mm and a wide of about 0.6 mm.

BRIEF DESCRIPTION OF THE FIGURES

FIGS. 2A-D illustrate exemplary embodiments of various fiber geometries.

FIGS. 4A-B illustrate the results of the study described in Example 2.

DETAILED DESCRIPTION

Figure 1:
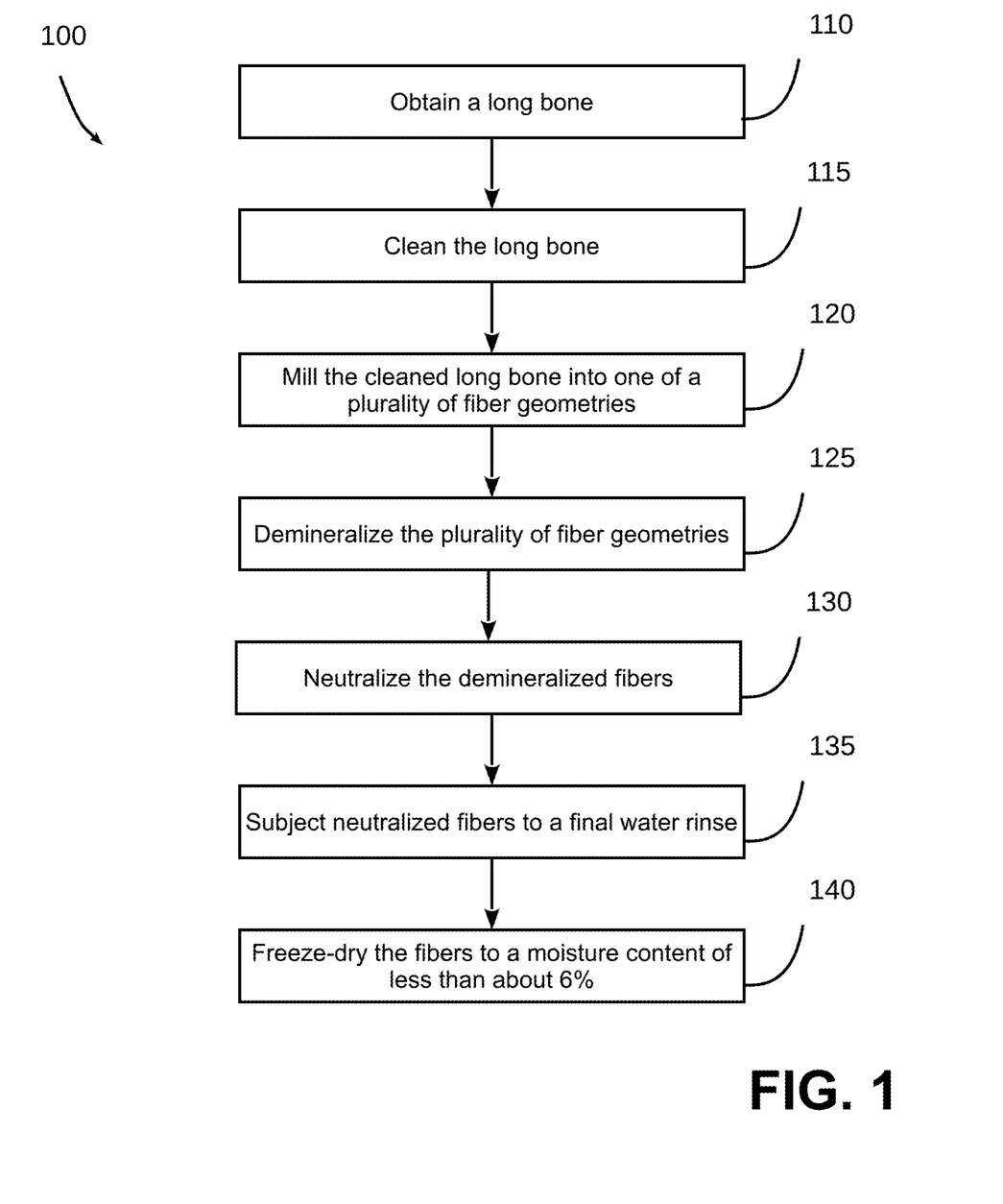
FIG. 1 is a flowchart of an exemplary embodiment of a method of obtaining a demineralized bone matrix having varying geometries.

With reference to FIG. 1, a method 100 of obtaining demineralized bone matrix of varying geometries is described. Generally, human cortical bone fibers are milled from long bones. In some instances, individual lots of fibers may be processed, where each lot is obtained from a single long bone donor. At block 110 a long bone may be obtained, for example from a tissue bank. Next, at block 115, the obtained long bone may be cleaned. This cleaning may include debridement and then processing with hydrogen peroxide, isopropyl alcohol, and water rinses of the cortical shaft segments; although, this is not intended to be limiting, other cleaning protocols known in the art may also be utilized.

At block 120 the cleaned cortical segments may then be milled to produce one of four different defined fiber geometries: (1) long narrow (LN); (2) long wide (LW); (3) short narrow (SN); and, (4) short wide (SW). Although the geometries provided herein are arbitrarily defined, they represent typical variation in fiber dimensions, and thus are a good representation of the varying geometry types. In some embodiments, this milling may be on a CNC (Computer Numeric Control) machine using a solid carbide 2-straight flute end mill. In some such embodiments, the milling on the CNC machine may range from about 1500 rpm to about 2500 rpm and with a feed rate of approximately 0.38 mm per circumferential pass. In other embodiments, the milling machine may operate at about 1500 rpm for milling wide fibers; and the milling may operate at about 2500 rpm for milling narrow fibers. Alternatively, the milling may be on a CNC machine using a solid carbide 4-straight flute end mill. It is to be understood that other conventional techniques for milling the cortical segments may be used, and that the milling techniques are not limited to the description of milling herein.

Figure 2A:
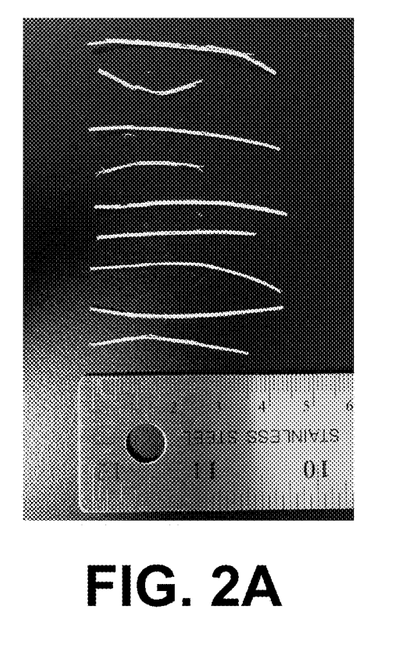
FIG. 2A illustrates an example of long narrow demineralized bone matrix fibers.

In some embodiments, the resulting long narrow (LN) fibers may have a length of approximately 10 mm or greater; in other embodiments, the long narrow fibers may be about 50 mm, or longer. The long narrow fibers may have a thickness ranging between about 0.2 mm to about 0.6 mm. FIG. 2A illustrates exemplary embodiments of DBM fibers of a long narrow geometry.

Figure 2B:
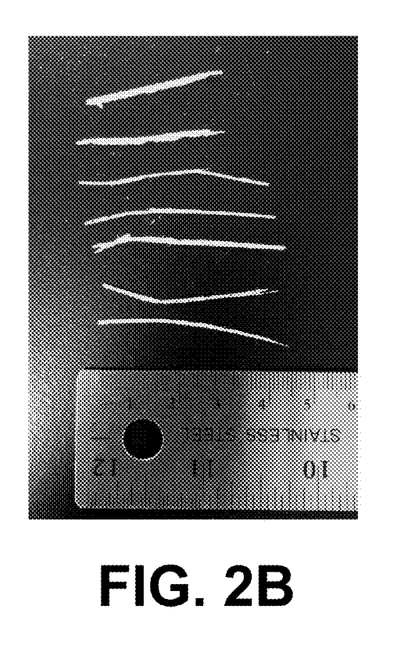
FIG. 2B illustrates an example of long wide demineralized bone matrix fibers.

In some embodiments, the resulting long wide (LW) fibers may have a length of approximately 10 mm or greater; in other embodiments, the long wide fibers may be about 50 mm long, or longer. The long wide fibers may have a width ranging between about 0.6 mm to about 1 mm, or more. FIG. 2B illustrates exemplary embodiments of DBM fibers of a long wide geometry.

Figure 2C:
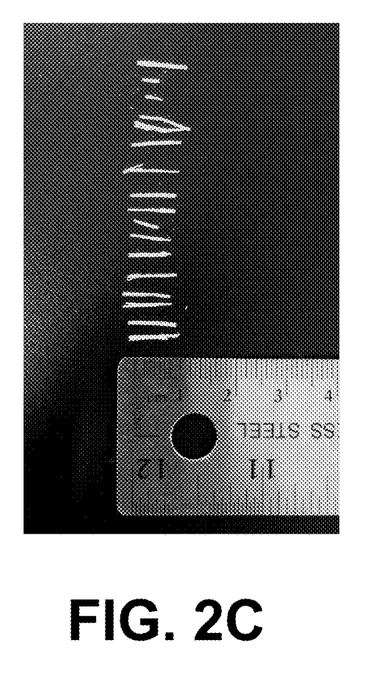
FIG. 2C illustrates an example of short narrow demineralized bone matrix fibers.

In some embodiments, the resulting short narrow (SN) fibers may have a length of less than about 10 mm. The short narrow fibers may have a width ranging between about 0.2 mm to about 0.6 mm. FIG. 2C illustrates exemplary embodiments of DBM fibers of a short narrow geometry.

Figure 2D:
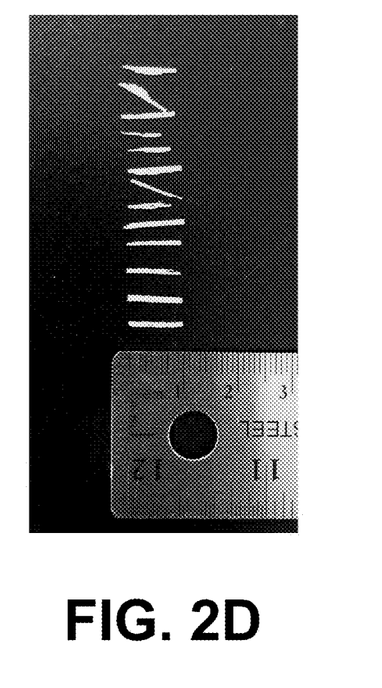
FIG. 2D illustrates an example of short wide demineralized bone matrix fibers.

In some embodiments, the resulting short wide (SW) fibers may have a length of less than about 10 mm. The short wide fibers may have a width ranging between about 0.6 mm to about 1 mm, or more. FIG. 2D illustrates exemplary embodiments of DBM fibers of a short wide geometry.

At block 125, the various geometry fibers (e.g. LN, LW, SN, and/or SW) may be demineralized. In some embodiments, this demineralization may take place in a reaction vessel utilizing 0.5 N hydrochloric acid, where approximately 40 ml HCl/gram of bone is used for approximately 5 to about 90 minutes. However, this is not intended to be limiting, as other demineralization methods, including higher or lower concentrations of hydrochloric acid, or other acids, may be utilized. Additionally, other methods known in the art may also be utilized to demineralize the fibers. At block 130, the demineralized bone fibers of varying geometries (e.g. LN, LW, SN, and/or SW) may be neutralized, for example by rinsing and/or buffering. In some embodiments, the rinsing may be with RO (reverse osmosis) or DI (deionized) water and the fibers may be rinsed about two to three times. In some embodiments, the demineralized bone of varying geometries may be buffered with a 0.1 M sodium phosphate buffer (pH 6.9). At block 135, the neutralized demineralized bone fibers may be subjected to a final water rinse, followed by a freeze-drying cycle (block 140) in order to achieve a moisture content of less than about 6% by weight. As the Examples below will demonstrate, the geometry of the DBM fiber may affect osteoinduction and osteoconduction levels. As demonstrated in the various Examples, DBM fibers with a narrow geometry may be better for osteoconduction than DBM fibers with a wide geometry. Furthermore, as shown in the Examples, long narrow DBM fibers may be considered the optimal for osteoconduction. With respect to osteoinduction, the Examples indicate, both in in vitro and in vivo studies, that DBM fibers with a wide geometry may be better for osteoinduction than DBM fibers with a narrow geometry. Furthermore, the Examples indicate, at least in vitro, that DBM fibers with a long geometry may be better for osteoinduction than DBM fibers with a short geometry. Overall, the Examples, collectively, indicate that DBM fibers with a long wide geometry may be better for bone formation than DBM fibers with a long narrow geometry.

As such, the resulting fibers may be used in order to increase the bone forming activity by optimizing the DBM fiber geometry for both osteoinductivity and osteoconductivity mechanisms of bone formation. In some embodiments, a composition of DBM made from different geometries of DBM fibers and/or particles may be utilized. More specifically, in some embodiments, a composition of DBM comprising a ratio of DBM fibers with a long wide geometry to DBM fibers with a long narrow geometry may be used, where the long wide fibers impart preferential osteoinduction and the long narrow fibers impart preferential osteoconduction. The ratio of long wide fibers to long narrow fibers may vary based on the intended use and effect of the DBM product. For example, the mixture may include a larger proportion of long wide fibers compared to long narrow fibers where the primary goal is osteoinduction; conversely, the mixture may include a larger proportion of long narrow fibers compared to long wide fibers where the primary goal is osteoconduction. For example, the ratio may be about 65:35 long wide to long narrow; although this is not intended to be limiting, as the ratio may vary from approximately 99:1 to approximately 1:99 depending on the desired properties of the final DBM product.

EXAMPLES

The resulting demineralized bone matrix fibers of varying geometries (LN, LW, SN, and/or SW) resulting from the above described methods may be used to evaluate both osteoconductivity and/or osteoinductivity in in vitro and in vivo studies.

Example 1

A rat spinal fusion model was used to test the four different fiber geometries described above (LN, LW, SN, and/or SW) for their osteoconductive properties. The DBM fibers (of all geometries) were deactivated using guanidine hydrochloride (GuHCl) to extract the growth factors from the DBM fibers prior to insertion. More specifically, the fibers were devitalized by exposure to 4 M guanidine hydrochloride for 16 hours, washed 6 times, and then freeze-dried. The deactivation of the GuCl was confirmed using a lot of DBM powder in a rat muscle pouch model at 28 days. Each sample was weighed to 40 mg+5 mg and hydrated with saline prior to its intermuscular implantation; samples were implanted between the gluteus superficialis and biceps femoris in the hind limb.

As described, a rat posterolateral fusion model was used in order to determine the effect of DBM fiber geometry on osteoconductivity. Implants consisted of 0.2 cc of deactivated DBM fiber material-either deactivated long narrow (LN-d) fibers, deactivated long wide (LW-d) fibers, deactivated short narrow (SN-d) fibers, deactivated short wide (SW-d) fibers, or DBM powder group (irregular particles sized between 125-850 µm). The study consisted of ten (10) rats per DBM group, with a total of 20 fusion masses or implant sites, where there was an implant site on each of the left and right posterolateral side. Each implant side received an implant volume of 0.2 cc.

Bone formation analysis was conducted via high resolution radiograph. Fusions were graded for the amount of bone formation on a three (3) point scale, where "0" indicates no bone formation; "1" indicates bone formation, but where the bone formation is limited to close proximity of the transverse processes (TP); and "2" which indicates extensive bone formation from TP to TP.

Figure 3:
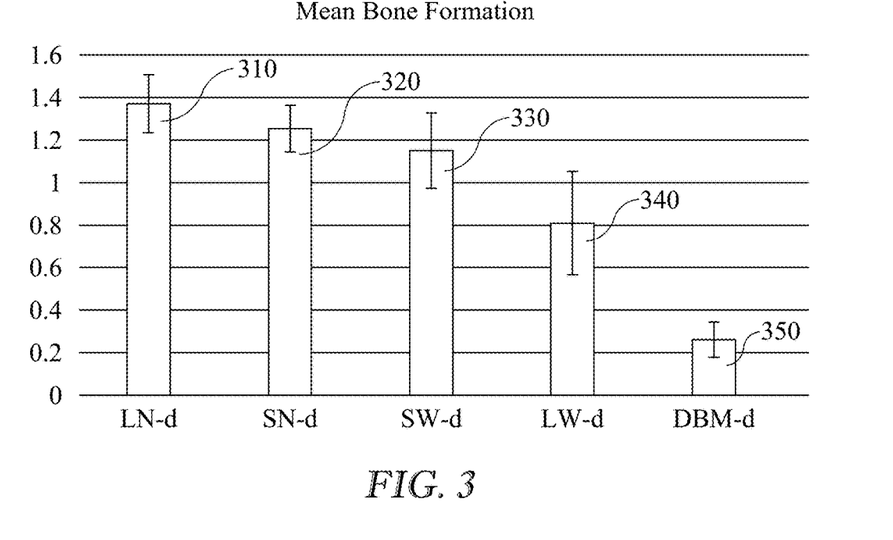
FIG. 3 illustrates the results of the study described in Example 1.

Table 1, below, and FIG. 3 illustrate the results of the study. Narrow fibers 310, 320 were found to outperform wide fibers 330, 340 (regardless of length). As shown in both Table 1 and FIG. 3, there was no obvious trend for the osteoconductivity related to the length (e.g. long versus short) of fibers. All geometries of the fibers outperformed the powder DBM group 350. Therefore, it may be concluded from this study that the osteoconductivity of DBM fibers may be greater than that of DBM powder. Furthermore, long narrow DBM fibers showed the greatest amount of osteoconductivity, and narrow DBM fibers were shown to be more osteoconductive than wide DBM fibers.

TABLE 1

| Group | Mean Score | Std. Dev. |
| --- | --- | --- |
| Long-Narrow (Deactivated) 310 | 1.37 | 0.14 |
| Short-Narrow (Deactivated) 320 | 1.25 | 0.11 |
| Short-Wide (Deactivated) 330 | 1.15 | 0.18 |

TABLE 1-continued

| Group | Mean Score | Std. Dev. |
| --- | --- | --- |
| Long-Wide (Deactivated) 340 | 0.81 | 0.25 |
| DBM Powder (Deactivated) 350 | 0.26 | 0.08 |

Example 2

Figure 4A:
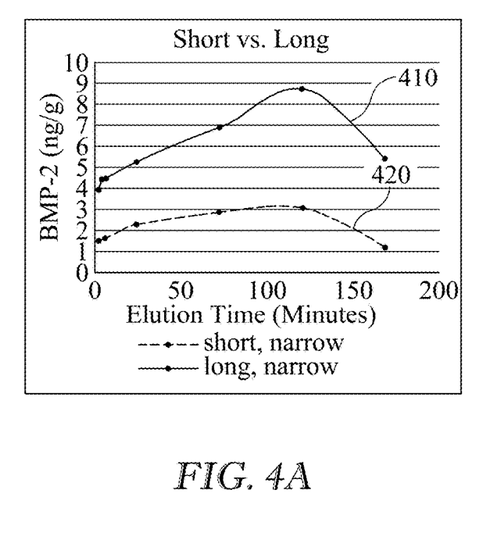
FIG. 4A illustrates a comparison between long DBM fibers and short DBM fibers.
Figure 4B:
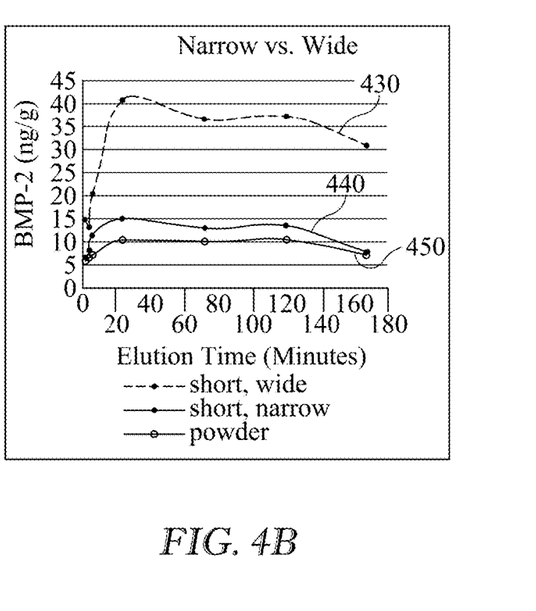
FIG. 4B illustrates a comparison between narrow DBM fibers and wide DBM fibers.

An in-vitro ELISA (enzyme-linked immunosorbent assay) for evaluating osteoinductivity was conducted. FIG. 4A illustrates the results of this study comparing long DBM fibers to short DBM fibers, while FIG. 4B illustrated the results of this study comparing wide DBM fibers to narrow DBM fibers. Referring now to FIG. 4A, fibers were prepared as described above from a single donor and were separated into long and short fibers with consistent width, e-beamed at 25-35 kGy, and tested for their BMP-2 elution versus time. A 1.5 g aliquot of sample was added to 19.5 ml of 200 mM HEPES buffer. Samples were then hydrated for 3 hours at 37° C. on a shaking water bath. Following hydration, collagenase at a concentration of 2020 u/mL was added to the samples, and the samples were incubated for up to 168 hours. Samples were vortexed and a 250 µl aliquot was taken and stored at −80 C for ELISA analysis at 0, 2, 4, 6, 24, 72, 120, and 168 hours. BMP-2 analysis was done utilizing the R&D Systems Quantikine BMP-2 ELISA, Tecan plate reader, and Magellan software. As illustrated in FIG. 4A, the long fibers 410 eluted more BMP-2 per gram of DBM than the short fibers 420.

Referring now to FIG. 4B, similar to above the DBM fibers were prepared from a single donor, and then were milled into narrow and wide fibers, with a consistent length. Fibers were tested for their BMP-2 elution vs time. Wide fibers 430 eluted more BMP-2 per gram of DBM fibers than narrow fibers 440. Based on this study, long wide fibers may possess the best BMP-2 elution characteristics, which is a marker for osteoinductive potential.

Example 3

A rat muscle pouch model was used to conduct an in vivo osteoinductive assay. Long DBM fibers of varying widths were prepared as described above for individual evaluation. In addition to the geometries described above (LN, LW) active DBM granules were evaluated; competitor products Grafton® Flex, DBX® Putty, and Optium® Putty were also evaluated. The selected material was implanted between the gluteus superficialis and biceps femoris muscles of an athymic rat in an amount of 0.1 cc. The implants remained in the animals for 28 days, after which the implants were analyzed via microCT imaging for bone formation and given an osteoinductivity (OI) score. The implants are given a score between 0 and 4. A score of 0 indicates no new bone forming elements detected, a score of 1 indicates 1% to 25% new bone forming elements, a score of 2 indicates 26% to 50% new bone forming elements, a score of 3 indicates 51% to 75% new bone forming elements, and a score of 4 (the highest score) indicates more than 75% new bone forming elements.

The results of the study are provided in Table 2 below. The activated long wide fibers (LW-a) performed the best, having the most new bone growth. Grafton® Flex performed second-best, closely followed by the active long narrow fibers. The ranking of material type by level of osteoinductivity continues as DBM-a granules, then distantly followed by DBX® Putty and Optium® Putty each of which failed to show much bone formation. In examining a pure osteoinduction model, DBM fibers with a long wide geometry performed better than DBM fibers with a long narrow geometry. This is consistent with the data obtained from the ELISA study presented in Example 2 above, which indicates that a wide geometry is preferred for osteoinduction).

TABLE 2

| Group | OI scores | Mean | Std. Dev. |
|---|---|---|---|
| LN-a DBF | 3, 3, 2, 2 | 2.5 | 0.6 |
| LW-a DBF | 4, 4, 4, 4 | 4.0 | 0.0 |
| DBM-a Granules | 3, 3, 2, 0 | 2.33 | 1.4 |
| Grafton Flex | 3, 3, 3, 3 | 3.0 | 0.0 |
| DBX Putty | 1, 0, 0, 0 | 0.25 | 0.5 |
| Optium Putty | 0, 0, 0, 0 | 0.0 | 0.0 |

Example 4

A rat spinal fusion model was utilized to evaluate combined osteoconductivity and osteoinductivity activity of the DBM fibers of the two most promising DBM fiber geometries (long wide and long narrow fibers) for their combined bone forming properties. The DBM fibers were tested in their final, active state. A total of six sample types were studied: (1) active long narrow DBM fibers (LN-a); (2) active long wide DBM fibers (LW-a): (3) active DBM powder with irregular particles between 125-850 µm (DBM-a); (4) Grafton® Flex; (5) DBX® Putty; and (6) Optium® Putty. The study consisted of eight to nine rats per sample type, each rat with two implant sites, one on each side (the left and right). Each implant side received an implant volume of 0.3 cc. Analysis of fusion was conducted by manual palpation and high resolution radiograph at 28 days post implantation. Volumetric analysis of total bone volume was conducted via microCT, also at 28 days post implantation. The results of this study are presented below in Table 3 and well as in FIG. 5.

Figure 5:
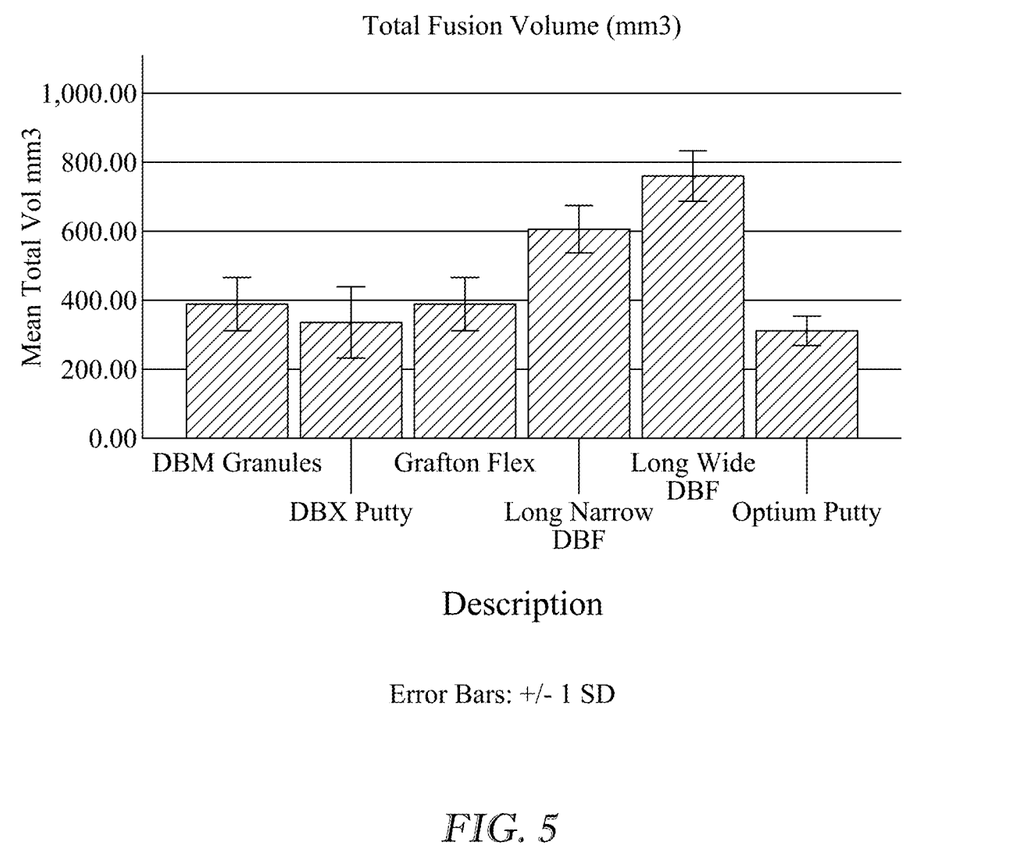
FIG. 5 illustrates the results of the study described in Example 4.

As shown in Table 3, treatment with DBM fibers with long narrow and long wide geometries resulted in 100% fusion, when evaluated by both manual palpation and radiograph; treatment with DBM powder also resulted in 100% fusion. Treatment with Grafton® Flex resulted in 88% fusion, when evaluated by manual palpation, and 94% fusion, when evaluated by radiograph. Treatment with DBX® Putty resulted in 50% fusion, when evaluated by manual palpation and by radiograph. Treatment with Optium® Putty resulted in 0% fusion, when evaluated by manual palpation, and 13% fusion, when evaluated by radiograph. This study illustrated no difference in fusion between the different DBM fiber geometries evaluated (long narrow and long wide). However, there were significant differences in bone volume between the long narrow DBM fibers and the long wide DBM fibers.

Referring now to the measurements of total bone volume taken via microCT, the bone volume for the long wide DBM fiber group (LW-a) was significantly higher than all other groups. Furthermore, the bone volume for the long narrow DBM fiber group (LN-a) was significantly higher than all groups, except in the long wide DBM group (LW-a). Based on this study, it may be concluded that DBM fibers with a wide geometry may result in greater bone volume and quality as compared to DBM fiber with a narrow geometry, and that DBM fibers with a wide or narrow geometry may result in greater bone volume and quality as compared to DBM powder. Furthermore, the long fiber geometries appeared to perform superiorly to the Grafton® Flex and the Optium® Putty, which contain shorter fibers therein.

TABLE 3

| Group | Fusion by Manual Palpation | Fusion by Radiograph | Total Bone Volume (mm3) |
|---|---|---|---|
| LN-a DBF | 9 of 9 | 18 of 18 | 606.59 (67.37) |
| LW-a DBF | 9 of 9 | 18 of 18 | 763.12 (68.22) |
| DBM-a Granules | 8 of 8 | 16 of 16 | 390.06 (75.64) |
| Grafton Flex | 7 of 8 | 15 of 16 | 388.13 (79.75) |
| DBX Putty | 4 of 8 | 8 of 16 | 336.24 (103.15) |
| Optium Putty | 0 of 8 | 2 of 16 | 314.91 (39.95) |

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of producing an osteoinductive and osteoconductive composition for in vivo use, the method comprising:
   obtaining bone tissue;
   cleaning the bone tissue obtained with a plurality of washes;
   milling the cleaned bone tissue into a plurality of fibers, wherein each fiber of the plurality of fibers has a geometry selected from:
      a long wide fiber, wherein the long wide fiber has a length of about 10 mm or greater and a width between about 0.6 mm and about 1.0 mm,
      a long narrow fiber, wherein the long narrow fiber has a length of greater than about 10 mm and a width between about 0.2 mm and about 0.6 mm,
      a short wide fiber, wherein the short wide fiber has a length of less than about 10 mm and a width between about 0.6 mm and about 1.0 mm, or
      a short narrow fiber, wherein the short narrow fiber has a length of less than about 10 mm and a width between about 0.2 mm and about 0.6 mm;
   demineralizing the plurality of fibers to expose one or more biologically active components;
   selecting a mixture of fibers from the plurality of fibers, wherein the mixture consists of a ratio of long wide fibers to long narrow fibers;
   combining the mixture of fibers to yield an osteoinductive and osteoconductive composition having osteoinductive properties and osteoconductive properties, wherein:
   the ratio comprises a larger proportion of long wide fibers to impart greater osteoinductive properties to the osteoinductive and osteoconductive composition, or
   the ratio comprises a larger proportion of long narrow fibers to impart greater osteoconductive properties to the osteoinductive and osteoconductive composition.

2. The method of claim 1, wherein the long wide fiber has a length between about 10 mm and about 50 mm, and a width of about 0.8 mm.

3. The method of claim 1, wherein the long narrow fiber has a length between about 10 mm and about 50 mm and a width of about 0.4 mm.

4. The method of claim 1, wherein the short wide fiber has a length of less than about 10 mm and a width of about 0.8 mm.

5. The method of claim 1, wherein the short narrow fiber has a length of less than about 10 mm and a width of about 0.4 mm.

6. The method of claim 1, wherein the ratio of the long wide fibers to the long narrow fibers is about 65:35.

7. The method of claim 1, further comprising freeze-drying the plurality of demineralized fibers of two or more geometries.

8. The method of claim 1, wherein demineralizing the plurality of fibers of two or more geometries includes treating the plurality of fibers with a hydrochloric acid treatment.

9. The method of claim 8, further comprising neutralizing the plurality of demineralized fibers of two or more geometries resulting in demineralized bone matrix.

* * * * *